US009693681B2

United States Patent
Nakajima et al.

(10) Patent No.: US 9,693,681 B2
(45) Date of Patent: Jul. 4, 2017

(54) OPHTHALMIC APPARATUS

(71) Applicant: Kabushiki Kaisha TOPCON, Tokyo-to (JP)

(72) Inventors: Masashi Nakajima, Tokyo-to (JP); Takaichi Tamura, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 0 days.

(21) Appl. No.: 14/764,013

(22) PCT Filed: Jan. 14, 2014

(86) PCT No.: PCT/JP2014/050872
§ 371 (c)(1),
(2) Date: Jul. 28, 2015

(87) PCT Pub. No.: WO2014/122966
PCT Pub. Date: Aug. 14, 2014

(65) Prior Publication Data
US 2015/0359424 A1 Dec. 17, 2015

(30) Foreign Application Priority Data
Feb. 6, 2013 (JP) .................. 2013-021725

(51) Int. Cl.
*A61B 3/10* (2006.01)
*A61B 3/15* (2006.01)
*A61B 3/00* (2006.01)

(52) U.S. Cl.
CPC .............. *A61B 3/10* (2013.01); *A61B 3/0025* (2013.01); *A61B 3/152* (2013.01)

(58) Field of Classification Search
CPC ........................ A61B 3/0075; A61B 3/0083
(Continued)

(56) References Cited

U.S. PATENT DOCUMENTS 4,817,620 A * 4/1989 Katsuragi .............. A61B 3/165
600/401
5,469,233 A * 11/1995 Katsuragi .............. A61B 3/165
351/205
(Continued)

FOREIGN PATENT DOCUMENTS

JP 2004-290286 A 10/2004
JP 2012-147835 A 8/2012
(Continued)

OTHER PUBLICATIONS

International Search Report and Written Opinion mailed Feb. 10, 2014 in corresponding PCT Application No. PCT/JP2014/050872.
(Continued)

*Primary Examiner* — Darryl J Collins
*Assistant Examiner* — Journey Sumlar
(74) *Attorney, Agent, or Firm* — Nields, Lemack & Frame, LLC

(57) ABSTRACT

An ophthalmic apparatus for measuring an ocular function in a non-contact manner, comprising two or more independent Z alignment detection systems for projecting an alignment light to an eye to be examined and detects a Z alignment position of the eye based on a reflection light from the eye and a control unit for controlling an alignment, wherein the Z alignment detection systems are adapted to have different magnifications, wherein the Z alignment detection systems project the reflection light from the eye to a common photodetection element and the control unit is adapted to execute a coarse Z alignment based on a signal obtained by a Z alignment detection system with a low magnification among the signals obtained from the photodetection element and to execute a precise Z alignment based on a signal obtained by a Z alignment detection system with a high magnification.

8 Claims, 2 Drawing Sheets

(58) Field of Classification Search
USPC .................................................. 351/208, 210
See application file for complete search history.

(56) References Cited

U.S. PATENT DOCUMENTS

| | | | |
|---|---|---|---|
| 2009/0195750 A1* | 8/2009 | Isogai | A61B 3/0075 351/208 |
| 2012/0249958 A1* | 10/2012 | Honda | A61B 3/152 351/206 |

FOREIGN PATENT DOCUMENTS

| | | |
|---|---|---|
| JP | 2012-213523 A | 11/2012 |
| JP | 2012-213524 A | 11/2012 |
| WO | 2012/144075 A1 | 10/2012 |

OTHER PUBLICATIONS

International Preliminary Report on Patentability mailed Aug. 20, 2015 in corresponding PCT Application No. PCT/JP2014/050872.

* cited by examiner

OPHTHALMIC APPARATUS

TECHNICAL FIELD

The present invention relates to an ophthalmic apparatus which measures an ocular function in a non-contact manner.

BACKGROUND ART

An ophthalmic apparatus is equipped with an alignment device which performs an alignment between an eye to be examined and a measurement optical system or an observation optical system in the ophthalmic apparatus.

Conventionally, in the alignment between the ophthalmic apparatus and the eye to be examined, an alignment light is projected to the eye to be examined, the reflection light from the eye to be examined is received by a photodetection element and the alignment is executed based on a photodetecting position of the reflection light.

For example, in the alignment (an X alignment or a Y alignment) in a direction (an X direction or a Y direction) orthogonal with respect to a measurement optical axis of the measurement optical system, the alignment light is projected to the eye to be examined from the measurement optical axis, the reflection light is received by the photodetection element, a deviation between the measurement optical axis and a photodetecting position is obtained on the photodetection element, and the measurement optical system is moved in the X direction and the Y direction so that the deviation is eliminated.

Further, in the alignment (a Z alignment) in a Z direction, the alignment light is entered with respect to the measurement optical axis at a predetermined angle and the reflection light is received, by the photodetection element. When the eye to be examined moves in a measurement optical axis direction, since the photodetecting position on the photodetection element changes according to a principle of optical lever, the measurement optical system is moved in the Z direction so that a deviation between an actual photodetecting position and a photodetecting position when aligned is eliminated.

It is to be noted that, since an accuracy of approximately 30 μm is required in the alignment in the Z direction, a coarse alignment optical system and a precise alignment system which has a higher magnification than the coarse alignment optical system are usually provided, the alignment is first performed in a predetermined range by the coarse alignment optical system, and a precise alignment is performed next by the precise alignment optical system.

The coarse alignment optical system and the precise alignment optical system are independent optical systems, photodetection elements for the coarse alignment and the precise alignment are provided respectively, an alignment light for the coarse alignment is emitted, the reflection light from the eye to be examined is received by the photodetection element for coarse alignment and the coarse alignment is executed, the processing is switched over to the alignment by the precise alignment optical system when fallen within a predetermined alignment range and the precise alignment is executed.

In a conventional alignment device, in a case of performing the alignment in the Z direction in particular, the coarse alignment and the precise alignment are performed respectively based on the signals from the different photodetection elements, i.e., the photodetection element for coarse alignment and the photodetection element for precise alignment. For this reason, it is necessary to perform a signal processing and a processing control for each of the photodetection element for coarse alignment and the photodetection element for precise alignment respectively, and hence a signal processing circuit becomes complicated. Further, since the signals from the different photodetection elements are switched over and then used, a simultaneousness of the signals become a problem. That is, a discontinuation of the signals occur while the signals are switched over, and a delay on a circuit occurs in association with the switching over of the signals.

For this reason, in a case where there is a change such as a movement of the eye to be examined, etc. in the switching over of the signals, for example, when blinking is performed and the like, a signal from the photodetection element or course alignment is greatly different from a signal from the photodetection element for precise alignment, and the coarse alignment cannot be shifted to the precise alignment. In such a case, the processing returns to the coarse alignment, the coarse alignment is performed again, and further, a process to shift to the precise alignment is carried out.

For this reason, conventionally, there was a problem that there is a case where the coarse alignment cannot be smoothly shifted to the precise alignment.

PRIOR ART REFERENCES

Patent Documents

Patent Document 1: Patent Publication JP-A-2004-290286
Patent Document 2: Patent Publication JP-A-2012-147835

SUMMARY OF THE INVENTION

Problem to be Solved by the Invention

To solve the problems as described above, it is an object of the present invention to provide an ophthalmic apparatus configured so as to smoothly shift from a coarse alignment to a precise alignment and efficiently perform an alignment operation.

Means for Solving the Problem

The present invention relates to an ophthalmic apparatus for measuring an ocular function in a non-contact manner, comprising two or more independent Z alignment detection systems for projecting an alignment light to an eye to be examined and detects a Z alignment position of the eye to be examined based on a reflection light from the eye to be examined and a control unit for controlling an alignment, wherein the two or more Z alignment detection systems are adapted to have different magnifications, wherein the two or more Z alignment detection systems project the reflection light from the eye to be examined to a common photodetection element and the control unit is adapted to execute a coarse Z alignment based on a signal obtained by a Z alignment detection system with a low magnification among the signals obtained from the photodetection element and to execute a precise Z alignment based on a signal obtained by a Z alignment detection system with a high magnification.

Further, the present invention relates to the ophthalmic apparatus, wherein the photodetection element has photodetecting areas corresponding to each Z alignment detection systems and each Z alignment detection system project reflection lights to corresponding photodetecting areas, wherein the control unit is capable of detecting a photodetection signal for each photodetecting area Further, the present invention relates to the ophthalmic apparatus, wherein the alignment lights of the two or more Z alignment detection systems have different wavelengths.

Further, the present invention relates to the ophthalmic apparatus, wherein a shielding member is provided at a boundary between two or more photodetecting areas formed on the photodetection element.

Further, the present invention relates to the ophthalmic apparatus, wherein the photodetection element is a line sensor and is capable of acquiring a positional information detected from each area and by a Z alignment detection system corresponding to each area in one scan of the line sensor.

Effects of the Invention

According to the present invention, an ophthalmic apparatus for measuring an ocular function in a non-contact manner comprises two or more independent Z alignment detection systems for projecting an alignment light to an eye to be examined and detects a Z alignment position of the eye to be examined based on a reflection light from the eye to be examined and a control unit for controlling an alignment, wherein the two or more Z alignment detection systems are adapted to have different magnifications, wherein the two or more Z alignment detection systems project the reflection light from the eye to be examined to a common photodetection element and the control unit is adapted to execute a coarse Z alignment based on a signal obtained by a Z alignment detection system with a low magnification among the signals obtained from the photodetection element and to execute a precise Z alignment based on a signal obtained by a Z alignment detection system with a high magnification. As a result, the simultaneousness of the signals obtained from the photodetection element in a case where the coarse Z alignment is switched over to the precise Z alignment can be ensured, and the shifting from the coarse Z alignment to the precise Z alignment can be carried out smoothly.

Further, according to the present invention, the photodetection element has photodetecting areas corresponding to each Z alignment detection systems and each Z alignment detection system project reflection lights to corresponding photodetecting areas, wherein the control unit is capable of detecting a photodetection signal for each photodetecting area. As a result, the reflection lights from the plurality of Z alignment detection systems are received respectively in different areas, and the signals from the photodetection element can be separated and obtained per each Z alignment detection system.

Further, according to the present invention, the alignment lights of the two or more Z alignment detection systems have different wavelengths. As a result, the alignment lights do not exert influence on each other and a detection result can be obtained per each Z alignment detection system.

Further, according to the present invention, a shielding member is provided at a boundary between two or more photodetecting areas formed on the photodetection element. As a result, the deterioration of a detection result due to a diffused reflection when photodetecting can be prevented.

Furthermore, according to the present invention, the photodetection element is a line sensor and is capable of acquiring a positional information detected from each area and by a Z alignment detection system corresponding to each area in one scan of the line sensor. As a result, positional information can be acquired easily and instantaneously.

MODE(S) FOR CARRYING OUT THE INVENTION

Description will be given below on embodiments of the present invention by referring to the attached drawings.

First, description will be given on an approximate arrangement of an ophthalmic apparatus for measuring an ocular function in a non-contact manner, according to FIG. 1 and FIG. 2.

Figure 1:
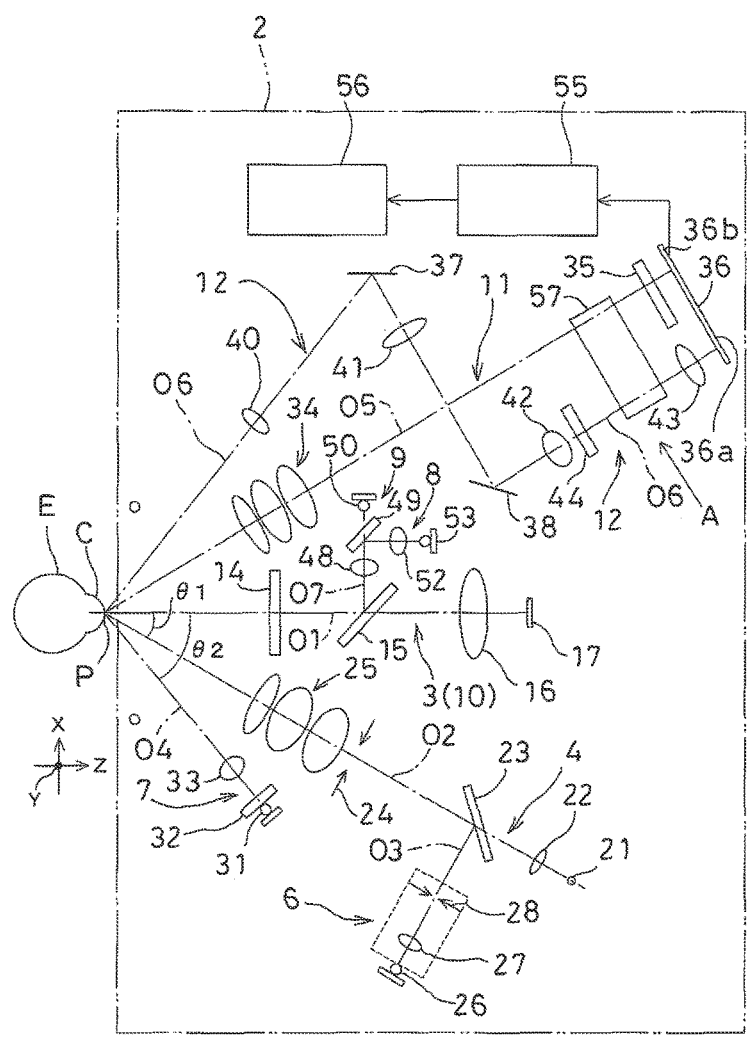
FIG. 1 is a schematic block diagram of a corneal endothelium photographing device according to an embodiment of the present invention.

In FIG. 1, a reference symbol E denotes an eye to be examined and a reference numeral 2 denotes an apparatus main body which is movable in directions of three axes X, Y, and Z. Inside the apparatus main body 2, there is provided an anterior ocular segment observation optical system 3, an illumination optical system 4 for photographing, a photographing optical system 5, a precise Z alignment projection system 6, a coarse Z alignment projection system 7, an XY alignment projection system 8, a fixation projection system 9, an XY alignment light receiving system 10, a precise Z alignment light receiving system 11, and a coarse Z alignment light receiving system 12. It is to be noted that the XY alignment light receiving system 10 and the anterior ocular segment observation system 3 are commonly shared. Here, the precise Z alignment projection system 6 and the precise Z alignment light receiving system 11 constitute a precise alignment detection system, the coarse Z alignment projection system 7 and the coarse Z alignment light receiving system 12 constitute a coarse alignment detection system and the XY alignment projection system 8 and the XY alignment light receiving system 10 constitute an XY alignment detection system.

A configuration will be further described.

In FIG. 1, the anterior ocular segment observation system 3 is disposed in accordance with each of the left and right eyes to be examined E, a main optical axis O1 of the anterior ocular segment observation optical system 3 is provided so as to coincide with an optical axis of the eye to be examined E respectively, and the main optical axis O1 is set so as to pass through an apex P of a cornea of the eye to be examined E.

On the main optical axis O1, a wavelength filter 14, a half mirror 15, an objective lens 16 and a photodetection element 17 are provided from the eye to be examined E side. A CCD element is used for the photodetection element 17, and the photodetection element 17 is disposed at a position conjugate to a cornea C of the eye to be examined E with regard to the objective lens 16.

The illumination optical system 4 for photographing is tilted at a predetermined angle with respect to the main optical axis O1, e.g. at an angle of θ1, has a projection optical axis O2 passing through the apex P, and an illumination light source 21 for photographing, a condenser lens 22, a dichroic mirror 23, an aperture stop 24 and an objective lens 25 is disposed on the projection optical axis O2 at a position distant from the eye to be examined E.

As the illumination light source 21 for photographing, for example, a xenon lamp for emitting a visible light or a light-emitting diode (LED) for emitting a green light, is used. The dichroic mirror 23 has a transmission characteristic which allows a transmitting of the visible light and reflects an infrared light, and the aperture stop 24 is disposed at a position conjugate to the cornea C with regard to the objective lens 25.

On a precise Z projection optical axis O3 branched by the dichroic mirror 23, the precise Z alignment projection system 6 has a light source 26 for precise Z alignment, a condenser lens 27 and a slit plate 28. The slit plate 28 and the cornea C are conjugate with regard to the objective lens 25. As the light source 26 for precise Z alignment, a light-emitting diode (LED) for emitting an infrared light, is used.

The alignment light emitted from the light source 26 for precise Z alignment is projected as a slit-like precise alignment light by transmitting through the slit plate 28. The precise alignment light is reflected by the dichroic mirror 23 and guided to the aperture stop 24, condensed by the objective lens 25 after transmitting through the aperture stop 24, and guided to the cornea C.

Therefore, the projection optical axis O2 along which the illumination light enters the cornea C and the precise Z projection optical axis O3 along which the precise alignment light enters the cornea C are common.

The coarse Z alignment projection system 7 is tilted at a predetermined angle with respect to the main optical axis O1, e.g. at an angle of θ2 (θ2>θ1), has a coarse Z projection optical axis O4 passing through the apex P, and a light source 31 for coarse Z alignment, a wavelength filter 32 and a condenser lens 33 are disposed on the coarse Z projection optical axis O4. The light source 31 for coarse Z alignment emits an infrared light as a coarse alignment light. A wavelength of the coarse alignment light is in a wavelength band different from chat of the precise alignment light, and a wavelength of the coarse alignment light and a wavelength of the precise alignment light are completely separated by the wavelength filter 32.

The precise Z alignment light receiving system 11 has a precise Z alignment optical axis O5, and the precise alignment optical axis O5 and the precise Z projection optical axis O3 (the projection optical axis O2) are symmetrical with respect to the main optical axis O1. Further, the precise Z alignment optical axis O5 is transmitted through the apex P.

On the precise Z alignment optical axis O5, an objective lens 34, a dichroic mirror 57, a wavelength filter 35, and a photodetection element 36 for alignment are provided, from the eye to be examined E side. It is so arranged that a precise alignment light reflected on the cornea C is condensed by the objective lens 34 and received by the photodetection element 36 for alignment through the wavelength filter 35. As the photodetection element 36 for alignment, a line sensor is used. The dichroic mirror 57 is adapted to reflect the visible light and transmit an infrared light. That is, the dichroic mirror 57 reflects the illumination light from the illumination light source 21 for photographing and transmits the precise alignment light and the coarse alignment light. The wavelength filter 35 transmits the infrared light emitted by the light source 26 for precise Z alignment. Further, the wavelength filter 35 has a transmission wavelength band different from that of a wavelength filter 44 to be described later.

A precise alignment light projected by the precise Z alignment projection system 6 is a slit light, and an optical system is constituted in such a manner that a condition where the precise alignment light is projected on the photodetection element 36 for alignment, the precise alignment light becomes orthogonal with respect to the photodetection element 36 for alignment.

The coarse Z alignment light receiving system 12 has a coarse Z alignment optical axis O6, and the coarse Z alignment optical axis O6 and the coarse Z projection optical system O4 are symmetrical with respect to the main optical axis O1. It is to be noted that, as a relationship between the precise Z alignment light receiving system 11 and the coarse Z alignment light receiving system 12, a magnification of the precise Z alignment light receiving system 11 is higher than that of the coarse Z alignment light receiving system 12, and a displacement of the apparatus main body 2 in the Z direction detected by the photodetection element 36 for alignment is arranged so as to appear large in the precise Z alignment light receiving system 11.

A first mirror 37 and a second mirror 38 are provided on the coarse Z alignment optical axis O6, the coarse Z alignment optical axis O6 deflected by the first mirror 37 and the second mirror 38 is made parallel to the precise Z alignment optical axis O5, and it is so arranged that the coarse Z alignment optical axis O6 enters the photodetection element 36 for alignment. Further, on the coarse Z alignment optical axis O6, relay lenses 40, 41 and 42 and an image forming lens 43 for forming an image of the coarse alignment light reflected by the cornea C on the photodetection element 36 for alignment, and a wavelength filter 44 provided between the relay lens 42 and the dichroic mirror 57 are provided.

A transmission wavelength band of the wavelength filter 44 is different from the transmission wavelength band of the wavelength filter 35, and it is so arranged that the precise alignment light and the coarse alignment light are completely separated by transmitting through the wavelength filter 35 and the wavelength filter 44.

Figure 2:
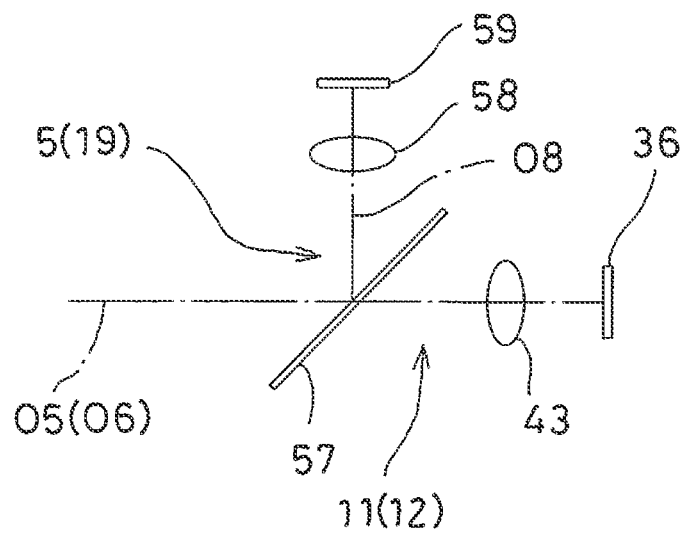
FIG. 2 is an arrow diagram A in FIG. 1.

As shown in FIG. 2, an image forming lens 58 and a photodetection element 59 for photographing are provided on an optical axis O8 branched by the dichroic mirror 57 and the illumination light reflected by the dichroic mirror 57 is adapted to be focused on the photodetection element 59 for photographing. The objective lens 34, the dichroic mirror 57 and the image forming lens 58 provided on the precise Z alignment optical axis O5 constitute the photographing optical system 5, and the photographing optical system 5 and the photodetection element 59 for photographing constitute an image pickup unit 19.

It is to be noted that the dichroic mirror 57 is used for transmitting a visible light and reflecting an infrared light and the photographing optical system 5 is provided on an optical axis branched by the dichroic mirror 57, but the photographing optical system 5 may be provided on the optical axis transmitted through the dichroic mirror 57 and the precise Z alignment light receiving system 11 and the coarse Z alignment light receiving system 22 may be provided on an optical axis branched or defected by the dichroic mirror 57.

Figure 3:
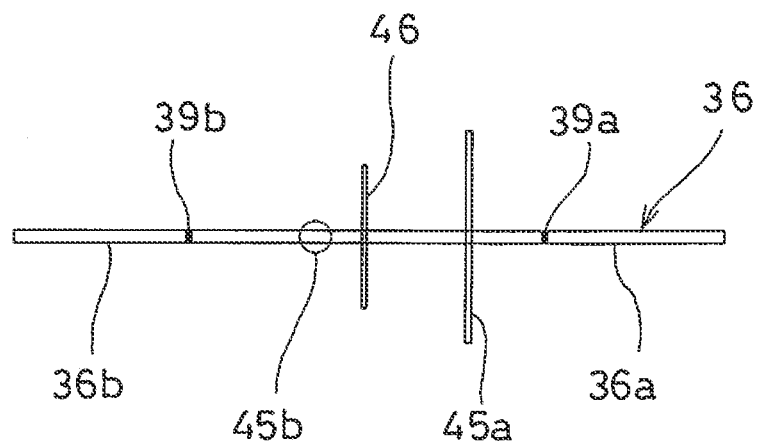
FIG. 3 is an explanatory drawing to show a relationship between a Z alignment photodetection element and a received alignment light in the corneal endothelium photographing device.

As shown in FIG. 3, the photodetection element 36 for alignment is divided into a photodetecting area 36a which receives a precise alignment light 45a and a photodetecting area 36b which receives a coarse alignment light 45b, and a shielding member 46 is provided at a boundary between the photodetecting area 36a and the photodetecting area 36b. The shielding member 46 is arranged so that a diffused reflection, when a reflection light is projected on both the photodetecting areas 36a and 36b, does not exert influence on the photodetecting condition of each of the photodetecting areas 36a and 36b. Further, the photodetecting area 36a and the photodetecting area 36b have a reference position 39a and a reference position 39b respectively, and the precise alignment light 45a and the coarse alignment light 45b are set in such a manner that the precise alignment light 45a and the coarse alignment light 45b coincide with the reference positions 39a and 39b respectively under a condition where the alignment of the apparatus main body 2 is complete in the Z direction with respect to the eye to be examined E.

The main optical axis O1, the projection optical axis O2, the precise Z projection optical axis O3, the coarse Z projection optical axis O4, the precise Z alignment optical axis O5, the coarse Z alignment optical axis O6 and the photodetection element 36 for alignment are arranged on the same plane.

The main optical axis O1 is branched by the half mirror 15, a relay lens 48 and a dichroic mirror 49 are provided on a branched optical axis O7, and a fixation light source 50 is provided on a passing through optical axis of the dichroic mirror 49.

A relay lens 52 and a light source 53 for XY alignment are provided on an optical axis branched by the dichroic mirror 49. In light source 53 for XY alignment, a light-emitting diode which emits a spot-like infrared light is used as an XY alignment light. The relay lens 52, the light source 53 for XY alignment, and de like constitute the XY alignment projection system 8.

The XY alignment, light projected from the XY alignment projection system 8 enters the cornea C through the main optical axis O1 and is reflected by the cornea C. The reflected XY alignment light is received by the photodetection element 17 via the main optical axis O1 and the anterior ocular segment observation optical system 3.

In the photodetection element 17, a reference position (an XY origin point) is set at a position where the main optical axis O1 passes through. Therefore, a case were a photodetecting position of the XY alignment light coincides with the reference position, is a condition where the alignment in the XY directions is completed. A deviation in the X direction and a deviation in the Y direction of the photodetecting position with respect to the reference position correspond to a deviation in the X direction and a deviation in the Y direction between a visual axis of the eye to be examined E and the main optical axis O1, respectively.

A result as photodetected by the photodetection element 36 for alignment is detected by an alignment detecting unit 55, and a detection result is output to a control unit 56. The control unit 56 controls a main body driving unit (not shown) based on the detection result, moves the apparatus main body 2 in the Z direction, and the alignment of the eye to be examined E and the apparatus main body 2 in the Z direction is executed.

A result as photodetected by the photodetection element 17 is detected by the alignment detecting unit 55 and the detection result is output to the control unit 56. The control unit 56 controls the main body driving unit (not shown) based on the detection result, moves the apparatus main body 2 in the XY directions, and the alignment of the eye to be examined E and the apparatus main body 2 in the XY directions is executed.

The alignment is carried out in a condition where the light source 26 for precise Z alignment and the light source 31 for coarse Z alignment are turned on and in a condition where the fixation light source 50 is turned on and the eye to be examined E is fixating the fixation light source 50.

A precise alignment light 45a is projected on the photodetecting area 36a of the photodetection element 36 for alignment via the precise Z alignment light receiving system 11, and a coarse alignment light 45b is projected on the photodetecting area 36b through, the coarse Z alignment light receiving system 12. Further, a precise alignment light and a coarse alignment light reflected by the cornea C are projected at the same time on the photodetecting area 36a and the photodetecting area 36b.

Further, the precise Z alignment light receiving system 11 and the coarse Z alignment light receiving system 12 have different magnifications, and both have different position detection ranges. That is, a detection position range in the Z direction corresponding to a photodetecting position information obtained from the photodetecting area 36a is small, and a detection position range in the Z direction corresponding to the photodetecting position information obtained from the photodetecting area 36b is large. Further, corresponding to a magnification, a large displacement amount in the Z direction can be detected based on a signal from the photodetecting area 36b but a detection accuracy is low, and a displacement amount in the Z direction, which can be detected based on a signal from the photodetecting area 36a, is small but a detection accuracy is high.

The alignment detecting unit 55 scans the photodetection element 36 for alignment, detects whether or not there is a photodetection signal from the photodetecting area 36a or the photodetecting area 36b. Since a case where the signal has been detected in the photodetecting area 36a shows a condition where the approximate alignment is completed, the alignment detecting unit 55 immediately executes a precise alignment based on the signal from the photodetecting area 36a. It is to be noted that a signal from the photodetecting area 36b can also be obtained when a signal can be detected in the photodetecting area 36a, but in a case where the signals can be obtained from both the photodetecting area 36a and the photodetecting area 36b, the signal obtained from the photodetecting area 36a is the first priority.

In a case where the alignment is not complete, a photodetecting position of the precise alignment light in the photodetecting area 36a deviates from the reference position of the photodetecting area 36a. Here, a condition where a position of the apparatus main body 2 in the Z direction is aligned at an appropriate position is a condition where the photodetecting position and the reference position coincide with each other.

The alignment detecting unit 55 detects a deviation between the photodetecting position and the reference position of the photodetecting area 36a and outputs to the control unit 56. The deviation from the reference position in the photodetecting area 36a can be taken as a positional information of the eye to be examined in the Z direction with respect to an ophthalmic apparatus.

The detected deviation is output to the control unit 56. The control unit 56 controls a main body driving unit, not shown, based on the inputted deviation and finely adjusts the position of the apparatus main body 2 in the Z direction.

When the apparatus main body 2 displaces in the Z direction, the photodetecting position of the precise alignment light displaces in the longitudinal direction of the photodetection element 36 for alignment. When the photodetecting position coincides with the reference position, the alignment in the Z direction is completed.

The alignment detecting unit 55 scans the photodetection element 36 for alignment, detects whether or not there is a photodetection signal from the photodetecting area 36a or the photodetecting area 36b, and executes a coarse alignment in a case where the signal has been detected only from the photodetecting area 36b.

A deviation between a photodetecting position of the coarse alignment light received by the photodetecting area 36b and the reference position set on the photodetection element 36 for alignment is detected by the alignment detecting unit 55 and the alignment detecting unit 55 outputs the detected deviation to the control unit 56. The control unit 56 controls the main body driving unit, not shown, based on the deviation and coarsely adjusts the position of the apparatus main body 2 in the Z direction.

When the alignment advances and the precise alignment light is received by the photodetecting area 36a, the alignment is switched over to an alignment based on the photodetection signal from the photodetecting area 36a. In this case, since the photodetecting area 36b in which the coarse alignment light is received and the photodetecting area 36a in which the precise alignment light is received are the same photodetection element, the synchronism at the time of the switching over can be assured and the signals from the same photodetection element are processed, a coarse alignment can be smoothly shifted to a precise alignment without an occurrence of a time lag with respect to signal processing.

Therefore, it is possible to omit an overlapping operation such as a restart from the coarse alignment due to a failure of the shift to the precise alignment from the coarse alignment, and an efficient alignment operation becomes possible.

It is to be noted that in the embodiment as given above, a line sensor is used as the photodetection element 36 for alignment, but a two-dimensional photodetecting sensor having an area may also be used.

Further, in an XY alignment, the alignment detecting unit 55 detects a deviation in the X direction and a deviation in the Y direction between the photodetecting position of the XY alignment light received by the photodetection element 17 and the reference position respectively, and an XY alignment is executed based on the deviations.

It is to be noted that, in the embodiment as given above, the two systems of the Z alignment light receiving systems are provided and configured so that respective alignments are independently detected, but it may be so arranged that three systems or three systems or more systems having different magnifications are provided, the alignment detection light guided by each of the Z alignment light receiving systems is received by one photodetection element for alignment, and arranged so as to assure a synchronism of the alignment signals obtained by each of the Z alignment light receiving systems.

LEGEND OF REFERENCE NUMERALS

2 Apparatus main body
3 Anterior ocular segment observation optical system
4 Illumination optical system for photographing
5 Photographing optical system
6 Precise Z alignment projection system
7 Coarse Z alignment projection system
8 XY alignment projection system
9 Fixation projection system
10 XY alignment light receiving system
11 Precise Z alignment light receiving system
12 Coarse Z alignment light receiving system
15 Half mirror
16 Objective lens
17 Photodetection element
19 Image pickup unit
21 Illumination light source for photographing
23 Dichroic mirror
26 Light source for precise Z alignment
28 Slit plate
31 Light source for coarse Z alignment
32 Wavelength filter
35 Wavelength filter
36 Photodetection element for alignment
36a Photodetecting area
36b Photodetecting area
44 Wavelength filter
50 Fixation light source
53 Light source for XY alignment
55 Alignment detecting unit
56 Control unit

The invention claimed is:

1. An ophthalmic apparatus for measuring an ocular function in a non-contact manner, comprising two or more independent Z alignment detection systems for projecting an alignment light to an eye to be examined and detects a Z alignment position of said eye to be examined based on a reflection light from said eye to be examined and a control unit for controlling an alignment, wherein said two or more Z alignment detection systems are adapted to have different magnifications and different tilt angles of optical axes with respect to an optical axis of said eye to be examined, wherein said two or more Z alignment detection systems project the reflection light from said eye to be examined to a common photodetection element and said control unit is adapted to execute a coarse Z alignment based on a signal obtained by a Z alignment detection system with a low magnification among the signals obtained from said photodetection element and to execute a precise Z alignment based on a signal obtained by a Z alignment detection system with a high magnification, and wherein said photodetection element has photodetecting areas corresponding to each Z alignment detection system and each Z alignment detection system projects reflection lights to corresponding photodetecting areas, and wherein said control unit is capable of simultaneously detecting a photodetection signal for each photodetecting area.

2. The ophthalmic apparatus according to claim 1, wherein the alignment lights of said two or more Z alignment detection systems have different wavelengths.

3. The ophthalmic apparatus according to claim 2, wherein a shielding member is provided at a boundary between two or more photodetecting areas formed on said photodetection element.

4. The ophthalmic apparatus according to claim 3, wherein said photodetection element is a line sensor and is capable of acquiring a positional information detected from each area and by a Z alignment detection system corresponding to each area in one scan of said line sensor.

5. The ophthalmic apparatus according to claim 2, wherein said photodetection element is a line sensor and is capable of acquiring a positional information detected from each area and by a Z alignment detection system corresponding to each area in one scan of said line sensor.

6. The ophthalmic apparatus according to claim 1, wherein a shielding member is provided at a boundary between two or more photodetecting areas formed on said photodetection element.

7. The ophthalmic apparatus according to claim 6, wherein said photodetection element is a line sensor and is capable of acquiring a positional information detected from each area and by a Z alignment detection system corresponding to each area in one scan of said line sensor.

8. The ophthalmic apparatus according to claim 1, wherein said photodetection element is a line sensor and is capable of acquiring a positional information detected from each area and by a Z alignment detection system corresponding to each area in one scan of said line sensor.

* * * * *